(12) United States Patent
Key

(10) Patent No.: US 6,746,444 B2
(45) Date of Patent: Jun. 8, 2004

(54) METHOD OF AMPLIFYING A BENEFICIAL SELECTIVE SKIN RESPONSE TO LIGHT ENERGY

(76) Inventor: Douglas J. Key, 12621 SW. Iron Mountain Blvd., Portland, OR (US) 97219

( * ) Notice: Subject to any disclaimer, the term of this patent is extended or adjusted under 35 U.S.C. 154(b) by 0 days.

(21) Appl. No.: 10/024,270

(22) Filed: Dec. 17, 2001

(65) Prior Publication Data
US 2002/0095143 A1 Jul. 18, 2002

Related U.S. Application Data

(60) Provisional application No. 60/258,006, filed on Dec. 20, 2000, and provisional application No. 60/256,555, filed on Dec. 18, 2000.

(51) Int. Cl.[7] .............................................. A61B 18/20
(52) U.S. Cl. ............................ 606/9; 128/898; 607/88
(58) Field of Search ........................ 606/9, 10; 607/88, 607/89; 128/898

(56) References Cited

U.S. PATENT DOCUMENTS

| 4,364,015 | A |   | 12/1982 | Drake et al. |        |
|-----------|---|---|---------|--------------|--------|
| 4,930,504 | A | * | 6/1990  | Diamantopoulos et al. | 607/88 |
| 5,290,274 | A | * | 3/1994  | Levy et al.  | 606/13 |
| 5,312,396 | A | * | 5/1994  | Feld et al.  | 606/11 |
| 5,540,676 | A | * | 7/1996  | Freiberg     | 606/3  |
| 5,620,478 | A | * | 4/1997  | Eckhouse     | 606/9  |
| 5,683,380 | A |   | 11/1997 | Eckhouse et al. |    |
| 5,720,772 | A |   | 2/1998  | Eckhouse     |        |
| 5,820,626 | A |   | 10/1998 | Baumgardner  |        |
| 5,873,875 | A | * | 2/1999  | Altshuler    | 606/10 |
| 5,885,273 | A | * | 3/1999  | Eckhouse et al. | 606/9 |
| 5,897,549 | A |   | 4/1999  | Tankovich    |        |
| 6,045,548 | A |   | 4/2000  | Furumoto et al. |    |
| 6,056,741 | A | * | 5/2000  | Van Saarloos | 606/5  |
| 6,074,382 | A | * | 6/2000  | Asah et al.  | 606/9  |
| 6,149,645 | A | * | 11/2000 | Tobinick     | 606/9  |
| 6,165,171 | A | * | 12/2000 | Tobinick     | 606/9  |
| 6,190,376 | B1 | * | 2/2001 | Asah et al.  | 606/9  |
| 6,208,673 | B1 | * | 3/2001 | Miyake       | 372/22 |
| 6,217,572 | B1 | * | 4/2001 | Tobinick     | 606/9  |
| 6,267,779 | B1 | * | 7/2001 | Gerdes       | 607/89 |
| 6,387,089 | B1 | * | 5/2002 | Kreindel et al. | 606/9 |
| 6,413,267 | B1 | * | 7/2002 | Dumoulin-White et al. | 607/89 |
| 6,428,532 | B1 | * | 8/2002 | Doukas et al. | 606/9 |
| 6,514,243 | B1 | * | 2/2003 | Eckhouse et al. | 606/9 |
| 2001/0001118 | A1 | * | 5/2001 | Asah et al. | 606/9 |

OTHER PUBLICATIONS

Bitter, *Dermatol. Surg.* 26:835–43 (2000).
Keller et al., *Lasers Surg. Med.* 20:32–38 (1997).
Weiss et al., *Dermatol. Surg.* 26:823–28 (2000).

\* cited by examiner

*Primary Examiner*—Lee Cohen
*Assistant Examiner*—Henry M Johnson, III
(74) *Attorney, Agent, or Firm*—Klarquist Sparkman, LLP

(57) ABSTRACT

A method of altering the appearance of a region of skin is disclosed. The method includes applying a sensitizing wavelength of light the region, and applying a treatment wavelength of light to the skin, wherein the treatment wavelength is a shorter wavelength than the sensitizing wavelength. The application of the sensitizing wavelength of light and the treatment wavelength of light results in a change in a physical property of the skin.

22 Claims, 19 Drawing Sheets

METHOD OF AMPLIFYING A BENEFICIAL SELECTIVE SKIN RESPONSE TO LIGHT ENERGY

PRIORITY CLAIMS

This claims priority to Provisional Patent Application No. 60/256,555, filed Dec. 18, 2000, and Provisional Patent Application No. 60/258,006, filed Dec. 20, 2000, both of which are incorporated by reference herein.

FIELD OF THE INVENTION

This invention relates to the field of skin treatment, more specifically to the use of light to change the appearance of the skin.

BACKGROUND OF THE INVENTION

As light energy is absorbed within the skin, light can be used to achieve desired clinical results. In particular, light has been used to remove hair, eliminate leg veins, remove or reduce the color of tattoos. In addition, water absorption of light energy transforming light into heat energy has been used for laser ablation of the skin surface or for use of lasers as cutting instruments. Plastic surgeons, dermatologists and their patients continually search for new and improved methods to alter the appearance of the skin.

Presently, all of the methods using either lasers or intense pulsed light in treating the skin require that the emitted energy to be absorbed selectively within the skin. The object that absorbs that energy, is termed a chromophore. The chromophore can be a true color such as black or brown, or red. Alternatively, this is a molecule absorbing energy, such as water or protein complex. Selective chromophore absorption is the absorption of a particular type of light energy by a chromophore. A clinical treatment can work because of selective chromophore absorption, wherein light energy is selectively absorbed by a particular component of the skin. If light energy were non-selectively absorbed throughout the skin, damage and injury would occur. The current problem in present laser and intense light treatment of the skin is that the clinical gain is often limited because the amount of beneficial skin selective chromophore absorption is always limited by the amount of non-selective unwanted absorption of energy throughout the skin.

SUMMARY OF THE INVENTION

The foregoing and other objects, features, and advantages of the invention will become more apparent from the following detailed description of a several embodiments which proceeds with reference to the accompanying figures.

A method of altering the appearance of a region of skin is disclosed. The method includes applying an effective amount of sensitizing wavelength of light to the region, and applying an effective amount of a treatment wavelength of light to the region, wherein the treatment wavelength is a shorter wavelength than the sensitizing wavelength. The application of the effective amount of the sensitizing wavelength of light and the effective amount of the treatment wavelength of light results in a change in a physical property of the skin.

In one embodiment, a method of beneficially altering the appearance of a region of skin is disclosed. The method includes applying sequenced complementary pulses of light energy, emitted from a laser or intense pulsed light source, to chromophore targets in the skin. There is a synergistic amplification of clinical response that results in a change in a physical property of the skin.

DETAILED DESCRIPTION OF SEVERAL EMBODIMENTS

Figure 1:
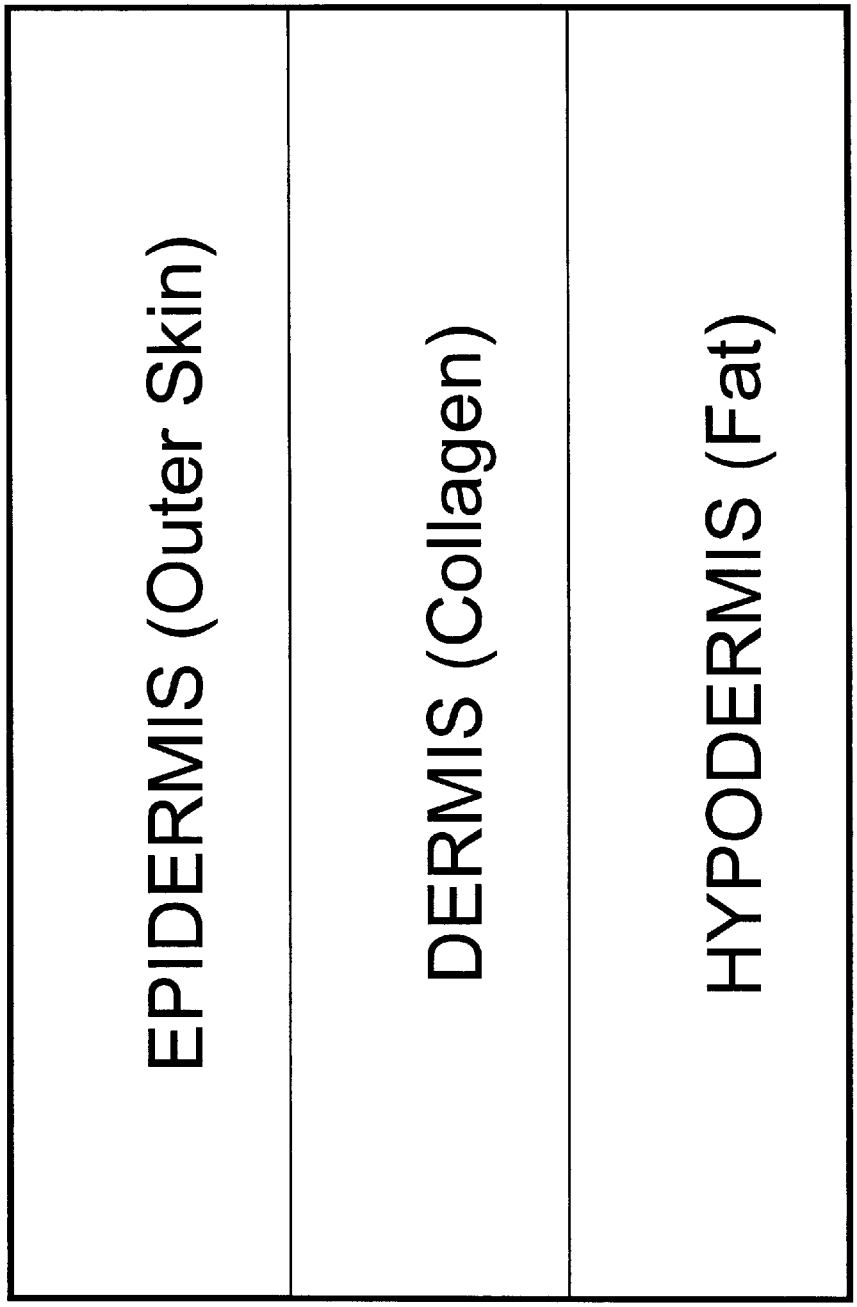
FIG. 1 is a schematic representation of the outermost layers of mammalian skin.
Figure 2:
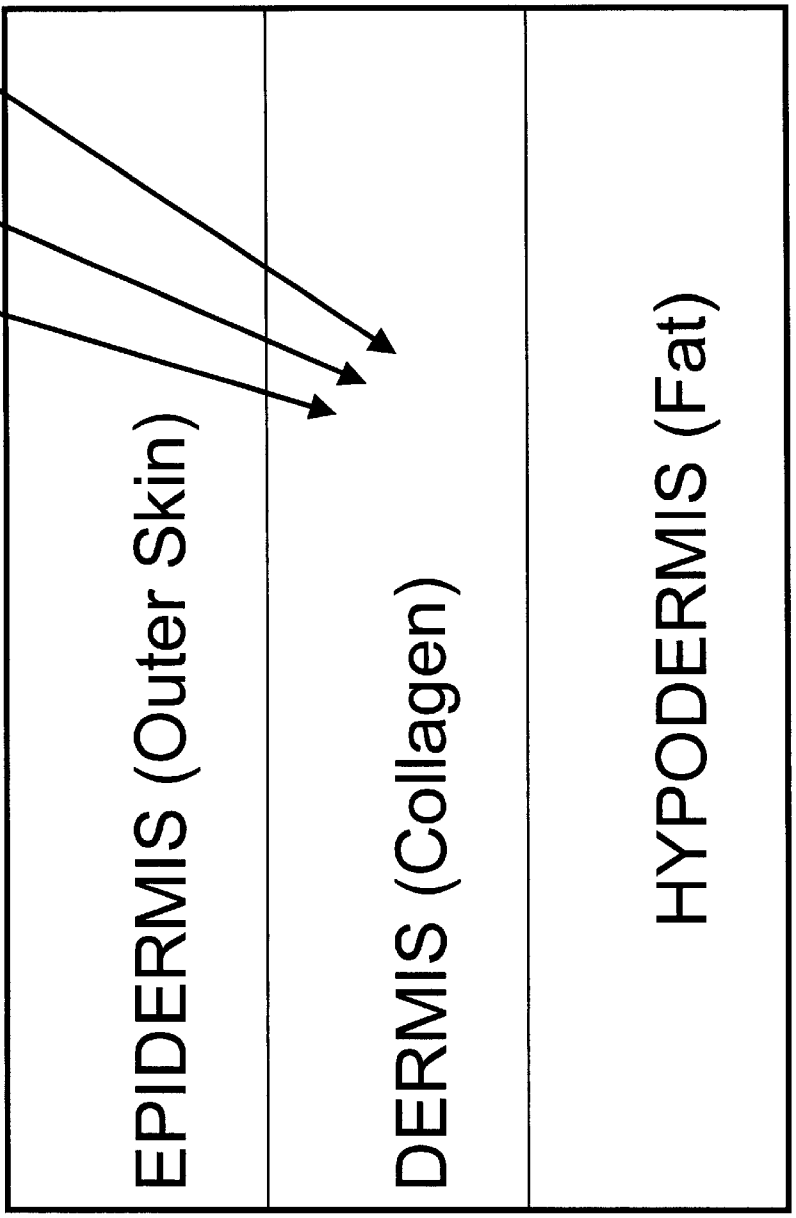
FIG. 2 is a schematic representation of a first pulse of infrared laser light. The light energy is absorbed by water molecules within the collagen layer of the skin. The pulse of infrared light energy reaches deeper into the skin than pulsed visible light or visible laser light.
Figure 3:
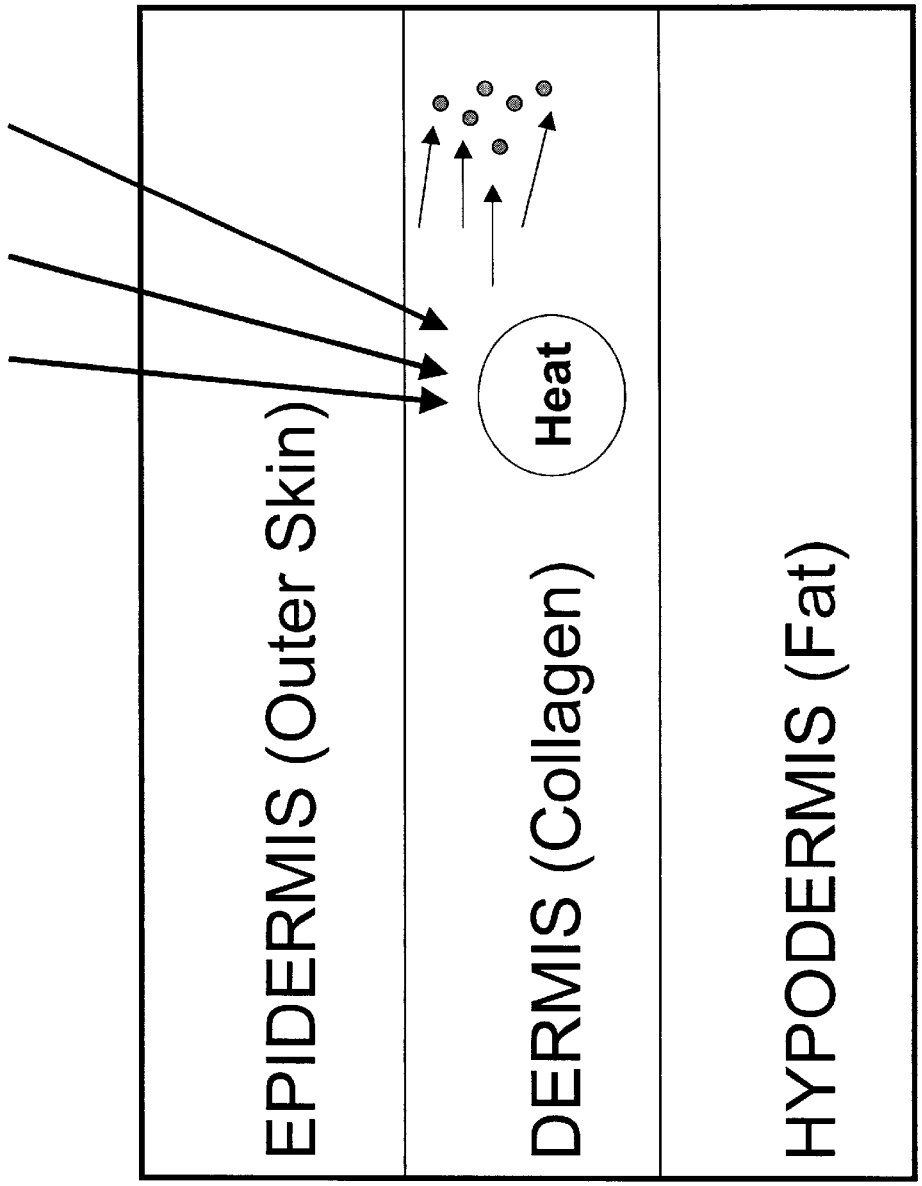
FIG. 3 is a schematic representation of transfer of this energy from the first infrared laser pulse into heat and blood vessel enlargement thereby increasing the size of smaller and deeper blood vessels in the collagen level of the skin.

The following disclosure and methods are provided to better define the present invention, and to guide those of ordinary skill in the art in the practice of the present invention. It must be noted that as used herein and in the appended claims, the singular forms "a", "an", and "the" include plural referents unless the context clearly dictates otherwise. Thus, for example, reference to "a cell" includes a plurality of such cells and reference to "the laser" includes reference to one or more lasers and equivalents thereof known to those skilled in the art, and so forth.

Unless defined otherwise, all technical and scientific terms used herein have the same meaning as commonly understood to one of ordinary skill in the art to which this invention belongs.

As discussed above, selective chromophore absorption of light can be limited during treatment of the skin. A chromophore is a chemical group that absorbs light at a specific frequency and so imparts color to a molecule. The reasons for the limitations on selective chromophore absorption of light energy are several. A common reason is that the chromophore presents too small of a target surface area so that light energy absorption is less than needed for the desired result. Alternatively, a given chromophore target my lie at a greater depth within the skin such that light energy is attenuated, thus the light energy absorption is less than needed for the desired result. The desired result of treatment may be either the elimination of that target or an inflammatory response elicited by energy absorption of that chromophore target. If the target chromophore initial response to an initial irradiance is not sufficient, and the energy absorption of the targeted chromophore is below a sufficient threshold response, then the desired biologic response can not be elicited. Irradiance is the density of radiation incident on a given surface usually expressed in watts per square centimeter or per square meter.

A greater target chromophore response is often desired and of definite biologic advantage. However, the present approach in use for treatment is to simply increase the initial irradiance. The logic of this present treatment is that more energy of like wavelength and kind delivered can reach a progressively smaller and perhaps deeper target chromophore area. However, the problem with this present approach to treatment is that at greater fluences of energy target specificity becomes less. As target specificity becomes less there is an increasingly greater chance of widespread injury in the surrounding skin because of nonselective energy absorption (as seen at higher irradiance). Nonselective energy absorption results in thermal injury to the surrounding tissues with increased risk of actual tissue injury, damage, and scarification (scar formation).

Thus, a method of amplifying skin and the appearance of the skin is provided by the methods described herein. The textural qualities of the skin can be improved, including brightness, clarity, smoothness, porosity, and translucency. Other qualities that can be measured include smoothness, pore size, telangiectasias, flushing, laxity, and dyschromic pigmentation. Additional and important qualities of the skin that can be subjectively and objectively measured include, but are not limited to skin laxity, or conversely skin tightness, and the presence and degree of textural fine lines and coarser lines within the skin.

These are the same qualities by which the external aspects of appearance (e.g. aging of skin) are judged. Improvement in these qualities by the method of treatment disclosed herein results in a benefit based on visual judgement of appearance. Changing a quality of the skin by the methods disclosed herein lessens the appearance of aging of the skin.

The methods disclosed herein utilize a sequence of irradiance of laser and intense pulsed light which are not identical, and are not a simple repetition, but are of irradiance of different nature and are complementary and additive in their tissue response. The use of the amplification of selective light energy absorption within the skin results in an increased benefit from the treatment and lessens the risk of injury by reason of non-selective energy absorption by the skin.

The sequences of laser and/or intense light disclosed herein are absorbed by the skin. The light energy is absorbed by the epidermis, the dermis, and/or the underlying hypodermis. Without being bound by theory, the sequence of laser and/or intense light pulses enhances the susceptibility of a chromophore within the skin or the adjacent connective tissue. The chromophore may be too small in its primary surface area, or too deep within the skin, or in its primary nature not have sufficient chromophore specificity, to achieve the desired effect with a single wavelength of light is applied. Thus, the enhanced susceptibility is due to a primary pulse of laser or intense light, termed a sensitizing wavelength of light. Following application of the sensitizing wavelength of light the enhanced target chromophore is susceptible to effective treatment with a second irradiance, termed a treatment wavelength of light. In one embodiment, the treatment wavelength is complementary intense pulsed light or a complementary laser pulse. The complementary intense pulsed light or laser pulse by itself, as a primary treatment, does not have sufficient therapeutic efficacy. It is only in combination with the sensitizing wavelength that the treatment wavelength is effective. Thus, the sequenced complementary laser and/or intense pulsed light irradiance amplify the desired chromophore response within the skin to achieve an enhanced therapeutic response.

The light sources used in the methods of the invention for either sensitizing irradiation or for amplification of a primary irradiated chromophore may either be a coherent or a non-coherent light source. A coherent light source is a source of light that is capable of producing radiation with waves vibrating in phase. The laser is one specific, non-limiting example of a coherent light source. In one embodiment, a coherent light source is an infrared laser, and a non-coherent light source is pulsed light that can be filtered (see Bitter, Dermatol. Surg. 26:835–43, 2000; Weiss et al. Bermatol. Surg. 26:823–28, 2000; Kelley et al., Lasers Surg. Med. 95:32–33, 1997).

Specific non-limiting examples of lasers of use with the methods disclosed herein include multiple infrared laser sources, pulsed dye lasers, and intense pulsed light. Infrared laser sources of use include, but are not limited to, the Vasculite laser™ at a wavelength of 1064 nm, the Cool Touch Laser™ (either the CoolTouch I™, see U.S. Pat. No.

5,820,626, or the CoolTouch II™, see U.S. Pat. No. 5,967, 123, CoolTouch Corporation, Roseville, Calif.)at 1320 and 1540 nm, and the Arameis erbium glass laser, a flash lamp-excited erbium glass laser (1.54 nm), Quantel Medicall, France (U.S. Pat. No. 5,897,549). The pulsed dye laser sources of use with the methods disclosed herein include, but are not limited to, the Photogenica V™ and V Star™ lasers (e.g. see U.S. Pat. No. 4,364,015 and U.S. Pat. No. 6,045,548, Cynosure, Inc. Chelmsford, Mass.) with use at both 585 and 595 nm. The intense pulsed light sources of energy use with the methods disclosed herein include, but are not limited to, the Photoderm Multilight™ (e.g. see U.S. Pat. No. 5,683,380 and U.S. Pat. No. 5,720,772, ESC/Sharplan (Lumenis), Norwood, Mass.) with spectral band of emission of filter intense pulsed light of between 515 nm and 1200 nm. In one embodiment, wherein a surface erythema primary response by reason of microabrasion is desired, one specific, non-limiting example of a light source of use is the Parisian Peel™ microabrasion system.

The spectral wavelength of coherent light laser sources as used may range from short wavelength visible light to extend into the long infrared wavelengths of about 1520 nanometers or longer. In one embodiment, the wavelength of the light is a short wavelength, or from about 500 nanometers (nm) to about 600 nm. In another embodiment, the wavelength of light is visible light, or from about 400 nm to 700 nm. In yet another embodiment, the wavelength of light is from about 600 nm to about 1320 nm, or from about 695 nm to about 1200 namometers.

In a further embodiment, the wavelength of light is a long wavelength, such as infrared light. Infrared light is light of the invisible spectrum, consisting of electromagnetic radiation with wavelengths in the range from 750 nanometers to 1 millimeter. One specific, non-limiting example of infrared light is light of about 1320 nanometers or longer. Another specific, non-limiting example of infrared light is the use of light emitted from a Nd:YAG laser of 1320 nanometers. The use of this spectrum is not limited, but may include as well shorter wavelength infrared emissions of 1040 nanometers. Without being bound by theory, this may be less efficient, possibly by reason of lesser diffusional absorption of this energy by water contained within the target tissue. In addition, longer wavelength light may as well be useful, provided that sufficient absorption in depth of the infrared laser energy is be achieved.

The pulsewidths used for both coherent and non-coherent light sources may range from about a nanosecond pulse to a long duration pulse of about 10, about 20, about 30, about 50 or about 100 milliseconds or longer. Pulsewidth is associated with the effective thermal relaxation time. In one embodiment, pulsewidth is associated with the cross-sectional dimension of the target chromophore. In addition, one of skill in the art can readily determine the spectral wavelength of light and the pulse duration based on the spectral absorption of the targeted chromophore, and the depth of the chromophore within the skin.

Without being bound by theory, the spectral wavelength of light is determined by the spectral absorption of the targeted chromophore, and relative depth of that chromophore within the skin itself. A therapeutically effective amount of light is the amount of light sufficient to affect, or to alter a property of, the target. One of skill in the art can readily determine the appropriate spectrum for a given chromophore, based on the absorption and emission spectrum of the chromophore. Thus, in one specific, non-limiting example, coherent laser light sources for chromophore amplification are used. Primary irradiation of the skin is performed with a sensitizing wavelength that targets a chromophore and prepares the skin for a treatment wavelength. In one embodiment, a sensitizing wavelength is an infrared wavelength. One specific non-limiting example of a sensitizing wavelength is emitted from an infrared laser source, of about 1320 nanometers. Without being bound by theory, shallow surface associated cooling allows for a dermal absorption of laser energy by reason of water absorption. This temperature elevation of the shallow to deeper collagen bearing part of the skin, the dermis, vasodilates small, threshold in sizes blood vessels within the skin. In one embodiment these vessels are capillaries.

A closely linked second laser sequence follows, termed the treatment wavelength. A therapeutically effective amount of the treatment wavelength provides the desired therapeutic result. In one embodiment, the second laser sequence follows within about 30 millisecond (msec) to about one minute, or from about 20 msec to about two minutes, or from about 10 msec to 1 second. In another embodiment, the second laser sequence follows within about two to about five minutes. In yet another embodiment, the second laser sequence follows within about five to about fifteen minutes. In a further embodiment, the second laser sequence follows within about fifteen to about thirty minutes.

In a further embodiment, there may be a delay sufficient to allow for a desired primary biological inflammatory response of several days. One specific, non-limiting example of an extended delay to allow for a primary biologic response is primary sensitizing treatment using either sclerosing injection or light irradiance of an unwanted area of leg veins insufficient in itself to eradicate this area of leg veins. This treatment is followed in a period of 2 to 3 days with a secondary light irradiance which is amplified in its response sufficient to give vessel disappearance (treatment). Without being bound by theory, vessel disappearance is due to the primary subthreshold induced inflammatory response. In this example sclerotherapy injection with hypertonic saline may be used as an example of primary treatment, with secondary delayed treatment being irradiance with infrared laser use at 1064 nm, with a pulse width of about 12 to 16 milliseconds, with fluences of use of between about 70 to 130 joules, as an example.

For example, primary treatment using either sclerosing injection or light irradiance of an unwanted area of leg veins, is followed in a period of 2 to 3 days with a secondary light irradiance at the treatment wavelength, which is amplified in its response by reason of the primary inflammatory response. In this embodiment the second laser sequence of pulsed laser light in the yellow to red lengths (treatment wavelength), may follow a primary laser irradiance of infrared emission (sensitizing wavelength). This sequence may be utilized, for example, in the treatment administered to the neck and or chest for improvement in both textural and coarser lines within the skin.

In one specific, non-limiting example, the primary sensitizing laser sequence of infrared laser light is between from about 690 nm to about 1520 nm, and the pulse duration is from below about 1 msec to about 20 msec. In this embodiment, the treatment laser sequence utilizes pulsed visible laser light in the yellow to red wavelengths. In one specific, non-limiting example, the visible laser light is between about 400 to about 700 namometers, or from about 500 to about 600 nanometers, and the pulse duration is from about a half of a millisecond to about several milliseconds. In one the embodiment, the pulse duration is from a range of about 250 nanoseconds up to about 100 milliseconds. One of skill in the art can determine the appropriate pulse duration. In general, the duration is from about a half of a millisecond up to about 40 milliseconds.

The treatment wavelength is a visible wavelength laser emission, or an intense pulsed light emission, pulsed over the same treated skin surface area as that of the primary infrared laser treatment. Without being bound by theory, this second irradiance is not targeted to, or absorbed by, the same chromophore as the first irradiance. Thus, in one embodiment, the second treatment irradiance is targeted to, and absorbed by, the dermal vasculature. The dermal vasculature has been enhanced in its laser visibility of absorption of energy, by reason of the primary infrared laser irradiance being absorbed nonspecifically by the water content of the dermal collagen. Accompanying the absorption is the release of heat and secondary dermal vasodilitation and inflammation. Without being limited by theory, the effects of the absorption of this secondary visible light laser treatment into the dermal enhanced vasculature is the release of inflammatory mediators that begin a process of restoration of the skin and reversal in particular of the photo-aging process.

Thus, in one embodiment, the primary dermal irradiance with the sensitizing wavelength is performed with the use of a more infrared biased cut off filter. In one specific, non-limiting example the infrared biased cut-off filter is a 755 nm or 695 nm cut-off filter, which allows the passage of light between the cut of 755 nm or 695 nm to about 1200 nm.

In one specific, non-limiting example, the infrared biased cut-off filter is a 755 nm or 695 nm cut-off filter, which eliminates more hemoglobin specific shorter wavelengths, and which still allows the passage of light of a spectrum between the cut of 755 nm or 695 nm up to 1200 nm. Without being bound by theory, this light is captured in the water and pigmented chromophore content of the collagen containing dermis of the skin. The capture of this energy transfers heat into the collagen layer, and results in vasodilation of smaller blood vessels within this skin area. A second intense pulsed light treatment then is performed within minutes of the first. In one embodiment this second treatment uses cut off filters which allow light which is preferably hemoglobin absorbed to pass through. These cut off filters often will range from 515 nm to 590 nm, and thus allow emission of light of greater than 515 nm or 590 nm. With these cut off filters the light of use is of shorter pulse widths of between 2 to 5 milliseconds. In one embodiment, this second treatment uses shorter cut off filters of 515 nm, 550 nm, or 570 nm and shorter pulse widths of a few milliseconds.

In one specific, non-limiting example, the sensitizing infrared irradiance of the dermis may be achieved by Nd:YAG laser emissions of either about 1320 or about 1040 nm. Without being bound by theory, this light is captured in the water and pigmented chromophore content of the collagen containing dermis of the skin. The capture of this energy transfers heat into the collagen layer, and results in vasodilation, and an enhanced secondary light capture target of smaller blood vessels within this skin area. The second pulse of light, the treatment wavelength, may then be targeted to the now enhanced vascular chromophore. This second treatment light emission may be irradiance with noncoherent intense pulsed light as described above or of a coherent laser light emission as described above, both of which are targeted to hemoglobin absorption in the now enhanced dermal microvasculature.

Without being bound by theory, this light is captured by the dermal vasculature that has been enhanced. Thus, the benefits of this treatment are two fold: (1) there has been a double reparative stimulus both of dermal damage and microvasculature damage; (2) there has been enhanced microvasculature damage, and by reason of this enhancement, enhanced stimulation of repair. Thus a method is disclosed herein wherein a sensitizing wavelength of light is applied to an area of the skin, followed by a treatment wavelength of light that is a shorter wavelength than the sensitizing wavelength.

The application of these two wavelengths can be separated by a brief recovery time period (see above). The application of both the sensitizing wavelength of light and the treatment wavelength of light results in a change of a physical property of the skin. Without being bound by theory, this process is additive not only by reason of the enhanced vascular chromophore response, but also because reparative responses to injury are multifold, both dermal absorption of infrared laser energy treatment and stimulation of a collagen reparative response, as well as an enhanced secondary irradiance and by reason of small domain blood vessel absorption of energy a separately stimulated skin repair by reason of injury to these same smaller in size blood vessels.

In one specific, non-limiting example, the methods and device described herein can be used to treat unwanted body hair. In this embodiment, primary treatment of body surface area designated for hair removal is first begun with the use of sensitizing wavelength emitted from a scanned Alexandrite laser, of about 755 nm, for about 2 to about 80 milliseconds pulse width. Without being bound by theory, this first irradiance is targeted to the hair follicle itself, with the target within the hair follicle being chromophore pigmentation. The energy of the first sensitizing irradiance is captured by the darker pigment within the hair follicle, and this energy is transferred as heat energy. The energy destroys the hair follicle and vasodilates the small dimensional blood vessels that surround and nourish the follicle. A second treatment wavelength from a coherent visible light source is applied to the skin following within minutes of the completion of sensitizing irradiance. Without being bound by theory, due to the secondary vasodilatation, this treatment wavelength can be targeted to, and be absorbed by, the small blood vessels surrounding the hair follicle, and thus remove these vessels.

The gain in effective treatment (e.g. hair removal) is a several fold increase, as compared to untreated skin. This method results in additive damage to the hair follicle, and more effective hair removal. In addition, there is a greater range of hair color response. Specifically, energy absorption by very light colored hair may be minimal, but by enhancing the visibility of small domain blood vessels around the hair follicle, the secondary laser treatment may well target hair of very light to minimal color.

Filtered intense pulsed light may be used in a similar manner by using pigmented hair treatment parameters initially. In one embodiment, a sensitizing wavelength is applied of about 645 nm or about 695 nm (using a cut off filter). The sensitizing wavelength is used with a chain of pulses of between 5 to 7 msecs, with minimal separation of 10 msecs. A secondary treatment pulse follows within minutes. This second treatment pulse uses a cut off filter of much shorter wavelength, such as about 550 nm or about 570 nm and a shorter pulse width of about 2 to about 4 msecs. Without being bound by theory, this second treatment pulse irradiates the secondarily dilated perifollicular vascular bed, and enhances or causes hair removal due to the damage and destruction of this vascular targeted chromophore.

Additional factors can be used to produce primary target chromophore enhancement; primary target chromophore enhancement does not have to be achieved by light irradiation alone. An example of this is the use of primary microabrasion of the skin surface to achieve, in the process of particle microabrasion, a secondary deeper dermal response of erythema. The induced dermal dilation of microvasculature then becomes an enhanced chromophore target for visible light, either a coherent laser source of light, or a noncoherent source of light such as intense pulsed filtered light. Examples of this process include the rejuvenation of the areas of the chest and neck, or arms and shoulders. These areas are primarily treated with superficial microabrasion to induce a fine dermal erythema, in order to dilate the dermal vasculature. Immediately following this primary procedure, irradiance with intense pulse filtered light is used as a sensitizing wavelength, with settings, for example, of about 515 nm, or about 550 nm, or about 590 nm, using a cut off filter. In this procedure pulsewidths of between about 2 to about 5 milliseconds are used. A chain of either a monopulse of light or a chain of pulses separated by only variables to allow for thermal relaxation of the epidermis. Thus, an emission of either a single pulse of noncoherent intense pulsed light or a train of pulses separated by an appropriate interval to allow for thermal relaxation of the pigment containing skin surface, can be utilized. These intervals between pulses usually range from between about 10 to about 40 milliseconds but may be longer for patients of darker skin color. This process increases the capture of this irradiated fluence by the dermal vasculature, which has been enhanced, vasodilated by the primary process of surface microabrasion.

In another embodiment, methods are disclosed herein to enhance pigmentation removal. One specific, non-limiting example is application of a therapeutically effective amount of a sensitizing irradiance with a coherent light source, such as an Alexandrite laser, emitting an irradiance of about 755 nm. In one example, this is of short pulse width such as about 10 to about 50 nanoseconds pulsewidth. In one specific non-limiting example, the primary sensitizing irradiance is of a pulse width between about 10 to about 100 nanoseconds. Without being bound by theory the light is captured in the pigmented melanosome choromophore within the skin surface area of pigmentation. The immediate response to this sensitization is often an intensification of the pigmented area due to inflammation and possible pigment darkening.

The first sensitizing irradiation is followed by a second treatment irradiation of both longer pulsewidth of several milliseconds and of a wavelength, which can be either specifically targeted to a pigment or is more vascular targeted (due to the induced inflammatory response). The secondary treatment follows within minutes after the first treatment. The secondary treatment can be with a coherent light source or with a non-coherent light source. In one embodiment, the non-coherent light source is the use of intense pulsed filter light. Intense pulsed filter light includes treatment with a cut off filter of about 550 to about 590 nanometers, and pulse widths of between about 2 to about 5 milliseconds. Either single or chained pulses can be used, allowing for thermal relaxation times of about 10 to about 40 milliseconds.

Figure 19:
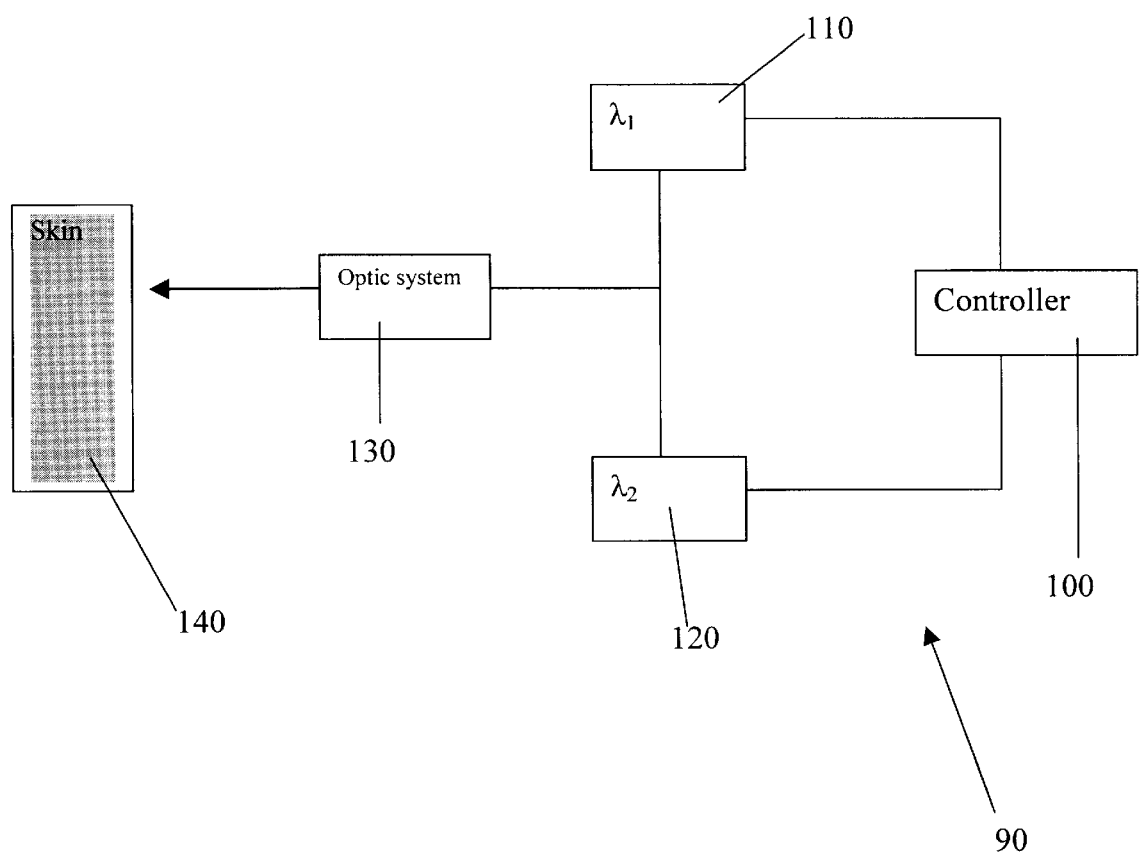
FIG. 19 is a schematic diagram of a device for the treatment of the skin that includes a controller 100 that controls two light sources ($\lambda_1$ 110 and $\lambda_2$ 120). Light emitted from these two light sources is directed to the skin 140 using an optic system 130.

As shown in FIG. 19, a system, including an apparatus generally indicated at 90, is of use for carrying out the described methods. The system includes a controller 100 for controlling the sequence of emissions from two light sources 110 and 120, such that first light source 110 and second light 120 source can be illuminated sequentially. In one embodiment, controller 100 also controls the wavelength emitted from light sources 110, 120. The first light source 110 is configured to provide a therapeutically effective amount of a sensitizing light flux; and a second light source 120 is configured to provide a therapeutically effective amount of a treatment light flux. The first and the second light sources can emit either coherent or non-coherent light. An optical system 130 directs the light emitted from light sources 110, 120 to a region 140 of the skin to be treated.

In one embodiment, first light source 110 emits infrared light, and is thus an infrared laser source. Infrared light sources include, but are not limited to an Nd:YAG laser. One of skill in the art can readily ascertain a suitable infrared laser source of use. For example, suitable laser sources are, but are not limited to, the Vasculite lasers at a wavelength of 1064 nm, the Cool Touch Laser™ (either the CoolTouch I™, see U.S. Pat. No. 5,820,626, or the CoolTouch II™, see U.S. Pat. No. 5,967,123, CoolTouch Corporation, Roseville, Calif.)at 1320 and 1540 nm, and the Arameis erbium glass laser. In a further embodiment, second light source 120 emits intense pulsed light. One of skill in the art can readily ascertain a suitable infrared source intense pulsed light.

In one embodiment, second light source 120 is a pulsed dye laser source. Suitable pulsed dye laser sources include, but are not limited to, the Photogenica V™ and V Star™ lasers (e.g. see U.S. Pat. No. 4,364,015 and U.S. Pat. No. 6,045,548, Cynosure, Inc. Chelmsford, Mass.) with use at both 585 and 595 nm. The second light source can also be an intense pulsed light source. These pulsed light sources include, but are not limited to, the Photoderm Multilight™ (e.g. see U.S. Pat. No. 5,683,380 and U.S. Pat. No. 5,720,772, ESC/Sharplan (Lumenis), Norwood, Mass.) with spectral band of emission of filter intense pulsed light of between 515 nm and 1200 nm.

In one embodiment, a least one controller 100 is provided that controls the first light source. This controller can be a computerized system, or can be a manual system (e.g. a switch). The controller can control both the first light source 110 and the second light source 120. Alternatively, more than one controller can be provided so that the first light source is controlled independently form the second light source.

In one embodiment, an optic system is provided 130 for delivering light to the skin. A single optic system can be provided that directs the light from both the first light source 110 and the second light source 120. In an alternative embodiment, more than one optic system can be included for directing light the light emitted by the light sources 110, 120. In one specific, non-liming example a first optic system directs the light from the first light source and a second optic system directs the light from the second light source to the skin.

The skin is affected by the devices and their methods of use disclosed herein to apply both the sensitizing and the treatment wavelength to the skin. The list of parameters that are altered using this process, and are considered indicative of a lessening and therein a reversal of the aging process, are a decreased in textural lines, coarser lines, or a change in skin laxity or skin tightness. In addition, the evenness of color of skin, observed with lessening of sun related pigmentation (i.e. dyschromic pigmentation) can be affected. Furthermore, skin exaggerated vascularity (such as telangiectasias and blush erythema) can be lessened, and the observed qualities of smoothness, softness, clarity luster, and brightness of skin can be improved Without further elaboration, it is believed that one skilled in the art can, using this description, utilize the present invention to its fullest extent. The following examples are illustrative only, and not limiting of the remainder of the disclosure in any way whatsoever.

EXAMPLES

Example 1

Experimental Use: Clinical Subjects

Several subjects were selected who had difficulties with brown age spots, uneven skin color, facial blood vessels, skin roughness, fine line and wrinkles, pore size and blush tone, and rosacea. Fifty-seven patients completed a sequence of five treatment sessions using pulsed light and infrared laser treatment. The sequence of five treatment sessions was performed between three and six week intervals. Prior to the treatment, ElaMax 5% cream was applied to the skin, followed by 1320 Nd:YAD laser treatment to the selected facial areas. The infrared light was applied using a 1320 Nd:YAD laser with linked dynamic cooling (Cool Touch Termescent laser system). A coolant interval of 20 msecs with a delay of 10 msecs was used. Fluences were adjusted to achieve a post-laser pulse skin temperature elevation of 40° C. The areas of select infrared laser treatment were periorbit, perioral, and selected areas of the forehead, cheek rhytides, and acne scars.

After the 1320 Nd:YAD laser treatment, filtered intense pulsed light was applied to the entire surface of the face (full facial treatment). Intense pulsed light was applied from a non-coherent flash lamp light source. The full facial application of light was over the areas of prior infrared laser treatment and over areas that had not specifically been treated before but where qualities of change would be textural. Cut off filters used between 550 and 590, with sequences of two pulses. The pulse width was between 2.4 and 5 msec. Shorter compression pulses of 2.4 msec were associated with purpurae. Longer pulse width settings (between 3 and 5 msec were initially used. Variables were adjusted and incremented for each treatment session, in order to achieve an endpoint of transient erythma, lasting several hours to overnight. Bruising was avoided by longer pulse width settings. Fluence settings ranged from 30 joules and were pulse width dependent.

The areas of select infrared laser treatment were the areas of greater line changes. Many of these line changes were lines of hyperdynamic expression.

Patients were asked to give a subjective judgement as to their response to treatment in a survey. Thirty-two patients completed survey.

A high subjective post treatment response was to skin textural qualities of both lessened blush tone erythema, telangiectasias, and photolentiginous solar pigmentation. This was seen as evenness of color tone, and described as increasing clarity of skin color. Increased skin tonal textural qualities as well as lessening of more defined periorbit and perioral deeper rhytides was seen, suggestive of an overall skin tightening response. Within the study group there was no adverse effects, or increased morbidity.

Figure 9:
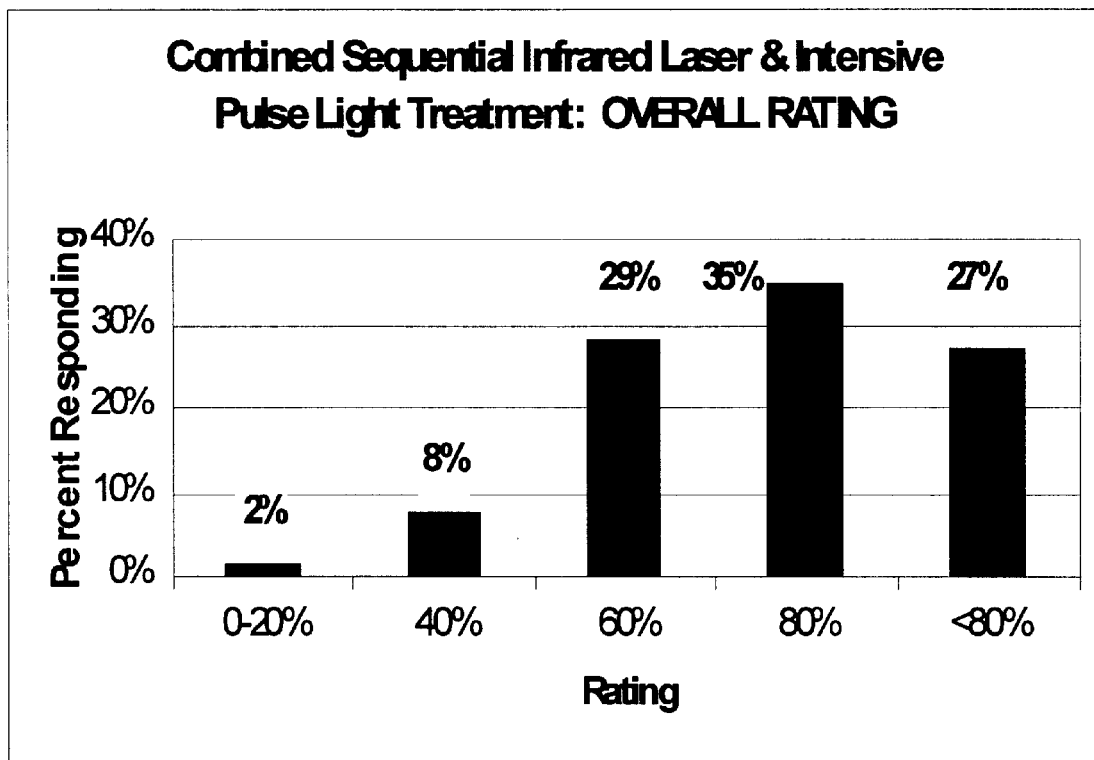
FIG. 9 is a bar graph showing the overall ratings of improvement in the skin with a first laser light pulse, followed by a subsequent pulse of visible light energy. Results shown are a rating by treated individuals, using defined parameters.
Figure 10:
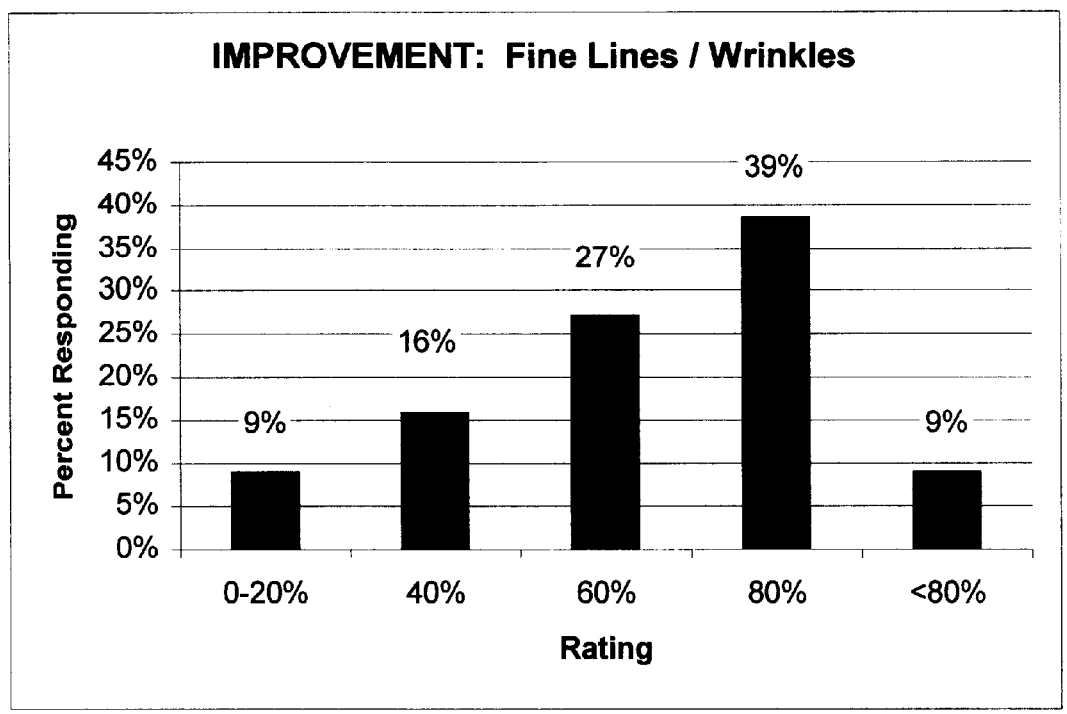
FIG. 10 is a bar graph showing the percent of improvement of fine lines and wrinkles responding to treatment. Results shown are a rating by treated individuals, using defined parameters.
Figure 11:
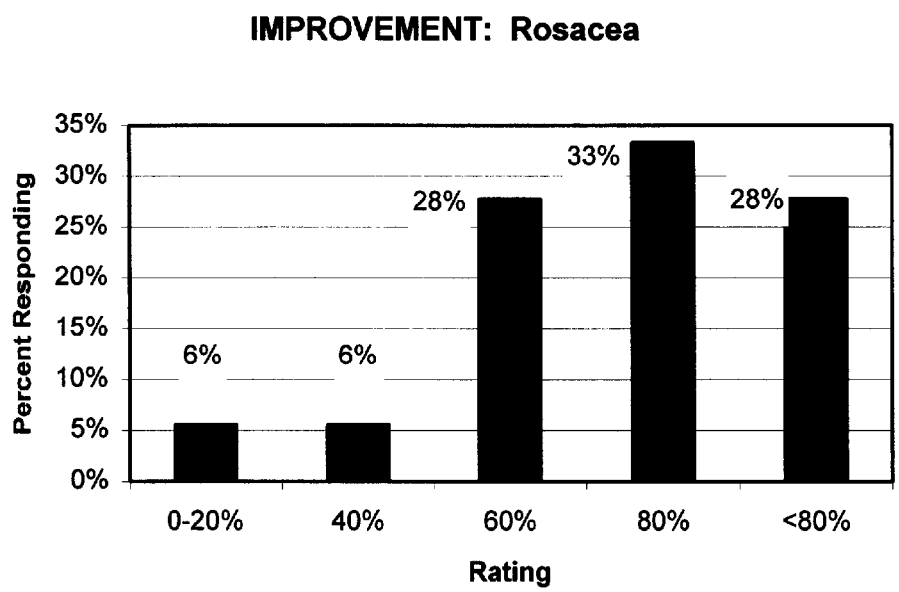
FIG. 11 is a bar graph showing the percent of improvement of rosacea. Results shown are a rating by treated individuals, using defined parameters.
Figure 12:
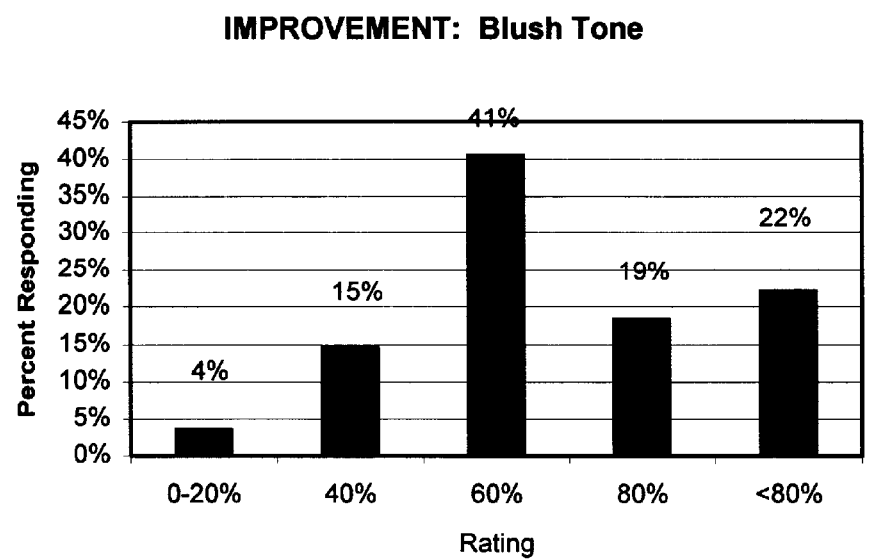
FIG. 12 is a bar graph showing the percent of improvement of blush tone. Results shown are a rating by treated individuals, using defined parameters.
Figure 13:
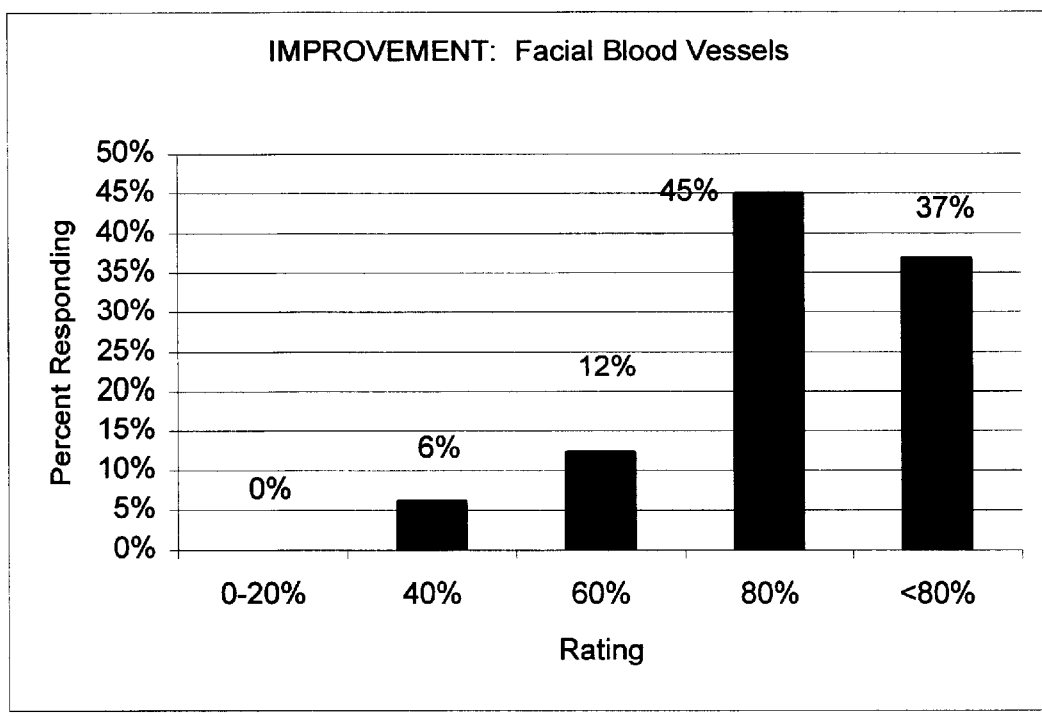
FIG. 13 is a bar graph showing the percent of improvement of facial blood vessels. Results shown are a rating by treated individuals, using defined parameters.
Figure 14:
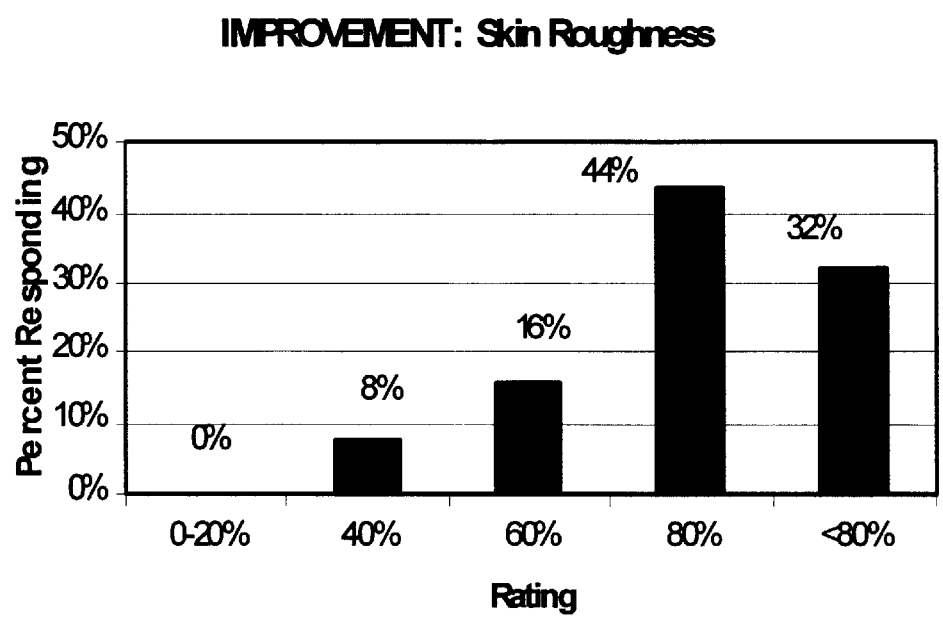
FIG. 14 is a bar graph showing the percent of improvement of skin roughness. Results shown are a rating by treated individuals, using defined parameters.
Figure 15:
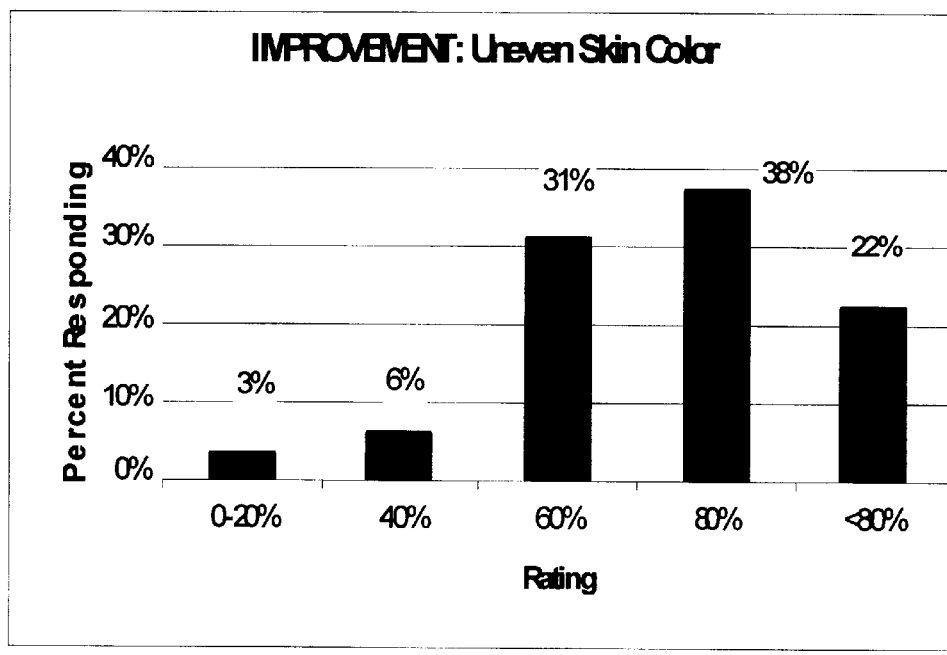
FIG. 15 is a bar graph showing the percent of improvement of skin color. Results shown are a rating by treated individuals, using defined parameters.
Figure 16:
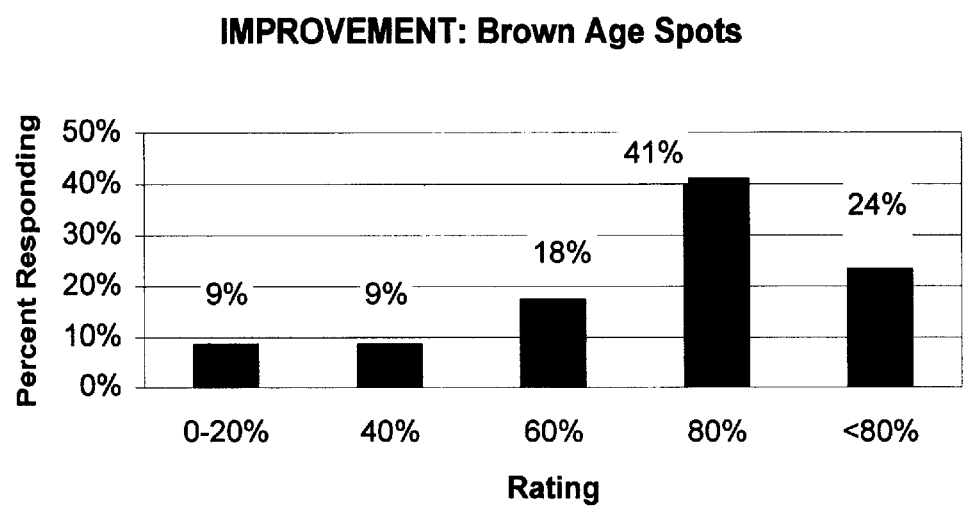
FIG. 16 is a bar graph showing the percent of improvement of brown age spots. Results shown are a rating by treated individuals, using defined parameters.
Figure 17:
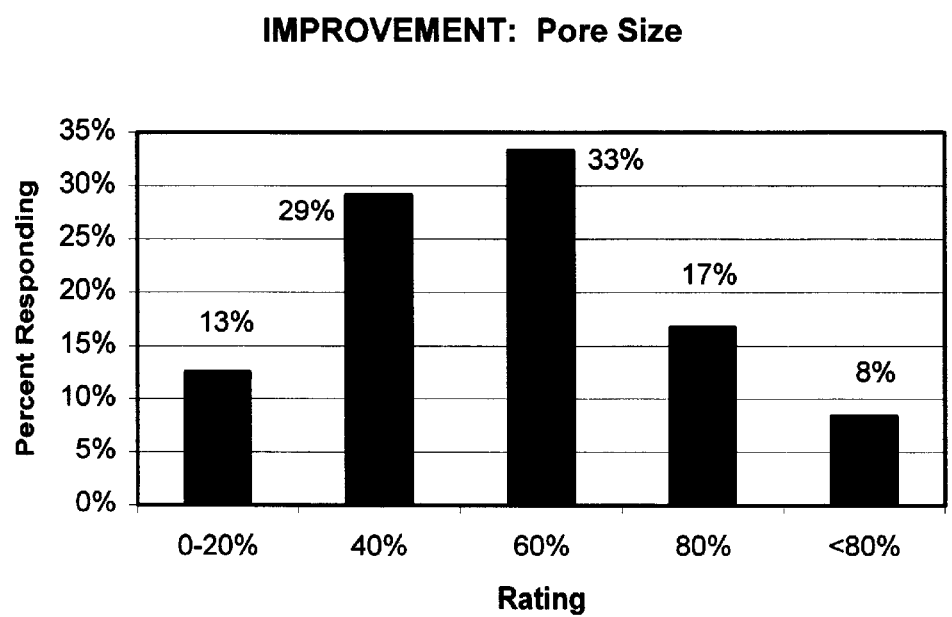
FIG. 17 is a bar graph showing the percent of pore size. Results shown are a rating by treated individuals, using defined parameters.

The results of the overall ratings of improvement in the skin is shown in FIG. 9. The results of the survey on facial lines are shown in FIG. 10. The results of the survey on rosacea are shown in FIG. 11. The results of the survey on blush tone are shown in FIG. 12. The results of the survey on facial blood vessel are shown in FIG. 13. The results of the survey on skin roughness are shown in FIG. 14. The results of the survey on skin color are shown in FIG. 15. The results of the survey on brown age spot are shown in FIG. 16. The results of the survey on pore size are shown in FIG. 17.

Example 2

Exemplary Protocol

In order to treat facial widespread sun-induced textural line change the following protocol is utilized. Primary treatment is infrared laser irradiance. This irradiance is to selected areas of more discrete line changes, such as around the mouth lines or around the eye lines, or is a full face application. An example of infrared laser irradiance treatment would be the use of the CoolTouch™ laser.

The treatment begins with cleansing of any prior existent skin emollients or lotions. Treatment is initiated with the CoolTouch™ I with settings of coolant spray duration of 20 msecs, delay of 30 msecs, with 18 to 20 joules with temperature measurement not to exceed 45 degrees. Alternatively, treatment with the upgraded Cool Touch II™ system is initiated with settings in a precool (i.e. coolant pulse first with laser pulse subsequent), mode of a coolant spray duration of 20 milliseconds (msecs), with fluences of between about 14 to 18 joules. A temperature monitored endpoint of between 40 to 45 degree Centigrade is achieved (temperature elevation). An accompanying endpoint is a transient but apparent skin erythema.

Over areas of more discrete line involvement at least two patterns of infrared laser irradiance are performed. With the Cool Touch II™ a third pattern of infrared laser irradiance is performed but in a post cool mode. Thus, a laser pulse is administered first with a coolant pulse post laser pulse. The settings are for a duration of coolant spray of 30 msecs with laser pulse fluences of 10 to 18 joules. Upon completion of infrared laser irradiance of the selected zones of treatment (i.e. peri-oral, peri-orbital or full face application, or as in the subsequent example the neck area for reasons of treatment of textural lines of skin aging change), a fine erythema is present as an appropriate endpoint of this first phase of treatment application.

The second phase of irradiance, following completion of the primary irradiance (see above), is treatment with intense pulse light. One specific, non-limiting example of a laser of use is the MultiLight™. Visible light irradiance is applied over the just completed areas of primary infrared irradiance treatment. In this secondary irradiance a present but fading erythema from the primary irradiance can still be present. The selected parameters of intense pulsed light treatment will vary as to the patients skin color and pigmentation. In one protocol, settings of treatment using intense pulsed light is a doublet pulse composed of a primary T1 pulse of 3 msecs, and T2 pulse of 4 msecs with a delay setting of 10 msecs, with a cut off filter inserted of 550 nm with fluences of between 32 to 40 joules. In another protocol, longer settings of between 4 to 6 msecs doublet pulses are used and lower cut off filters are used of 515 nms. The desired endpoint clinically observed as to treatment is a fine erythema. The treatment is applied over the areas of primary infrared laser irradiance.

Example 3

Treatment of Textural Lines on the Face and Neck

Another exemplary protocol example would apply to the treatment of textural lines on the face and neck. Primary irradiance is infrared irradiance using either the parameters of the above described CoolTouch I or II protocol over an area of about 120 mm². Alternatively infrared irradiance erbium glass laser irradiance is used with triplet pulses to quintuplet pulses with linked cooling with fluences of between 10 to 12 joules, or about 0.08 to about 0.1 joules/mm². The secondary irradiance with visible light is provided with treatment with the V Star Laser™ (see above) or Photogenica Laser™ (see above) at settings of 585 nm, 0.5 msecs pulse duration, and with a 10 mm spot size, fluences of between 2.5 and 3.0 joules (or about 0.02 to about 0.25 joules/mm²). Car e is taken to avoid a purpuric or bruising response. In one protocol, two sequences of laser pass patterns in this manner are used over the treatment field.

Results of improvement of textural and coarser lines, is measured both objectively and subjectively by photographic documentation as well as laser profilometry. An important determinant of response is observation over time to extend at least 6 months after completion of the series of active treatment.

Example 4

Clinical Results

In order to compare the additive advantages of primary sensitizing treatment with an infrared laser irradiance in combination with a closely sequenced treatment irradiance with a visible light emission pulsed dye laser the following study was performed. The results obtained were compared with irradiance with pulsed dye laser treatment alone.

The right and left half neck areas to be treated were randomized as to either combined treatment or pulsed dye laser only treatment. The Cool Touch II™ laser (see above) was used as an infrared source laser for irradiance of the randomized right or left neck areas. Settings were set for irradiance at 14 to 18 joules, at a pre-cool duration of 20 msecs, with a post-cool irradiance at 14 to 16 joules at a post cool duration of 30 msecs. A fine but short lived erythema was sought as a clinical endpoint of sensitizing treatment with post treatment peak temperature elevations not in excess of 43 degrees centrigrade.

Immediately post completion of randomized right or left neck infrared irradiance, confluent, both right and left neck areas were treated with 585 nm pulse dye laser visible light irradiance, at 0.5 msecs pulse duration, with a 10 to 12 mm spot size at 2.5 to 3.0 joules of energy. Three independent treatment sessions were given at 4 week intervals, with the above observation as to judged differences in bilateral treatment response as observed at 5 months post initiation of the first treatment.

Figure 18:
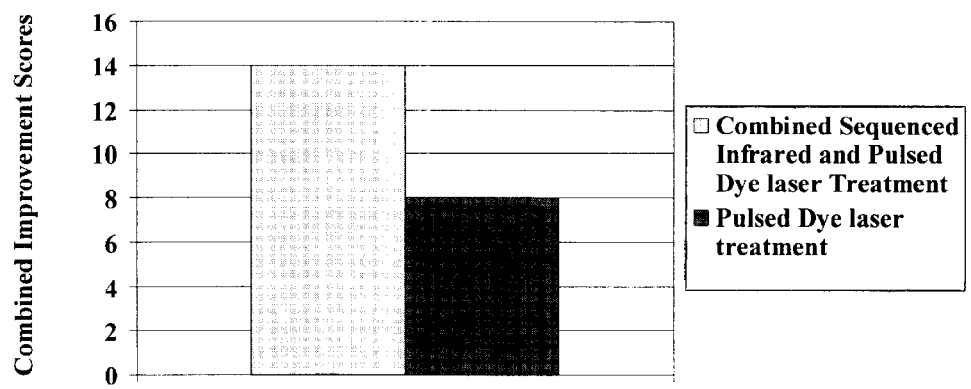
FIG. 18 is a bar graph showing the combined improvement scores for treatment of the neck.

The results shown in FIG. 18 reflect the cumulative scores as to improvement of textural lines and limited coarser line change of judged patient improvement both objectively and subjectively. Previous results have demonstrated that infrared laser irradiance alone has not given equivalent scores of clinical improvement. Similarly, equivalent scores of textural improvement were documented with the pulse dye laser only treatment in a comparison study of randomized right and left lateral cheek and face pulse dye laser treatment versus no treatment. No patients who objectively or subjectively showed improvement on the pulsed dye laser treated half neck area demonstrated an effect greater than the combined treatment side.

This results from this clinical study demonstrates the syngergistic effect seen with combined primary dermal infrared sensitizing irradiance with secondary visible light treatment irradiance. In this clinical example the primary sensitizing irradiance with the Cool Touch II™ infrared laser gave a synergistic amplification of a beneficial clinical response when followed in close sequence by V Star™ (see above) pulsed dye visible light irradiance.

Figure 4:
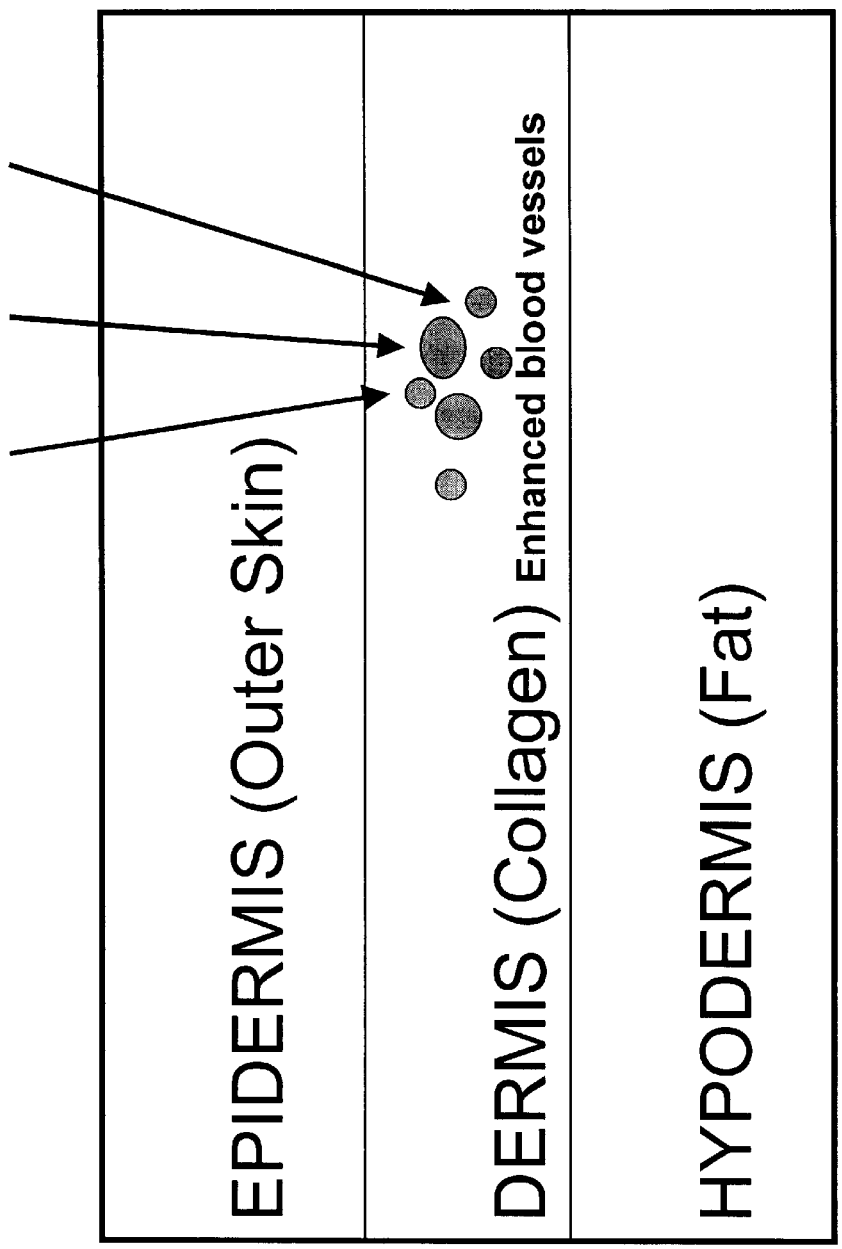
FIG. 4 is a schematic representation of a pulse of visible light energy on the skin. The energy can be emitted either from a laser or intense pulsed light source. This light energy reaches into the collagen level of the skin and is captured by smaller blood vessels, which were augmented by a first infrared light energy pulse.
Figure 5:
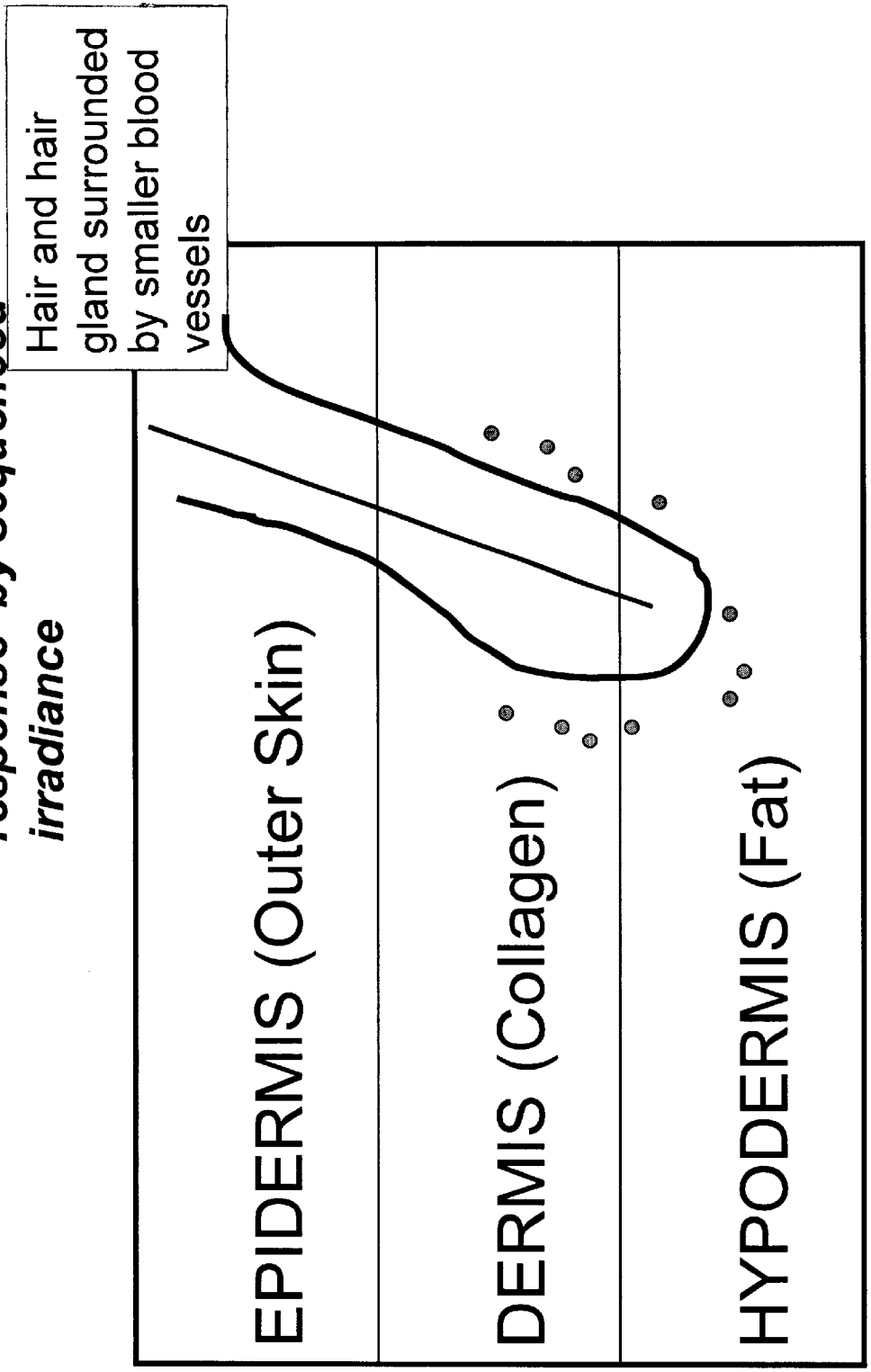
FIG. 5 is a schematic representation of the outermost layers of mammalian skin, including a hair and a hair gland within the skin, with surrounding smaller blood vessels that nourish the hair gland.
Figure 6:
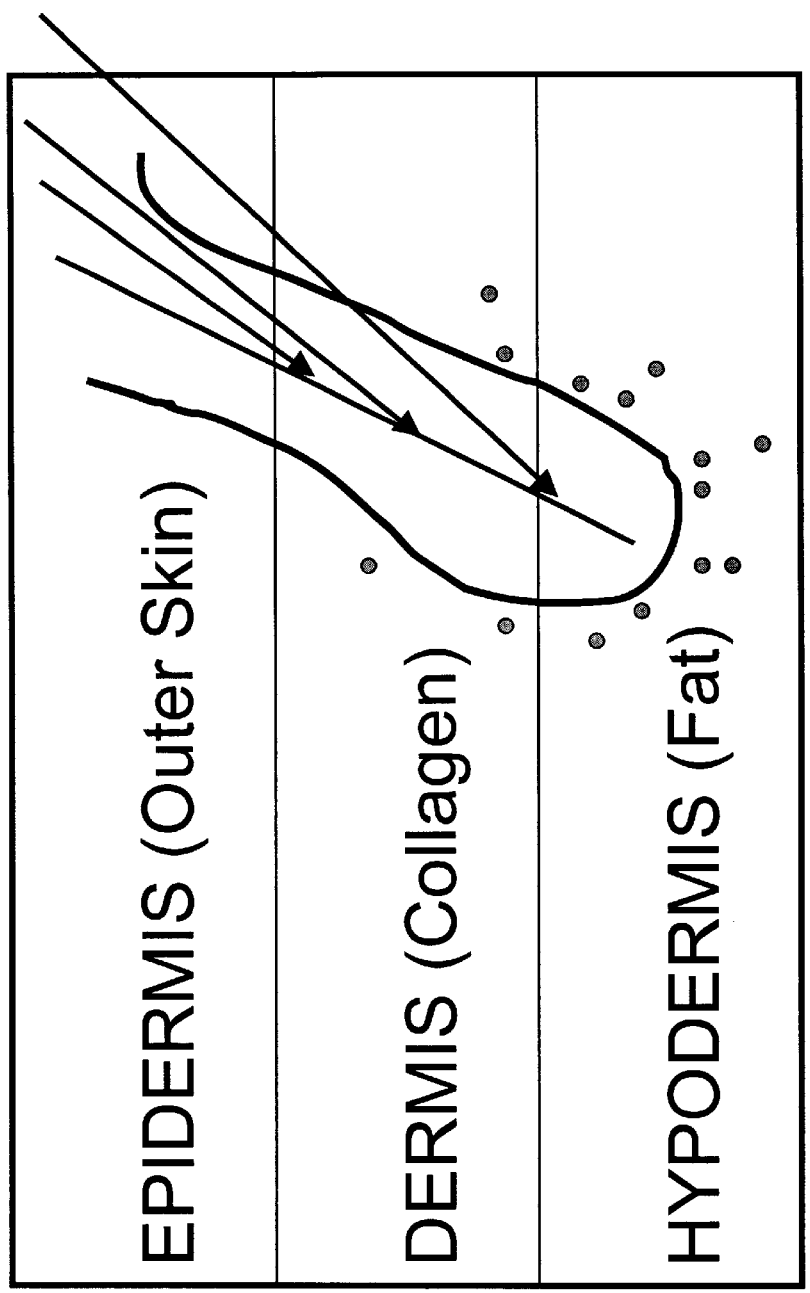
FIG. 6 is a schematic representation showing a primary first pulse of light energy from either a laser or intense pulsed light source that penetrates into the skin and is absorbed by the pigment chromophore within the hair gland.
Figure 7:
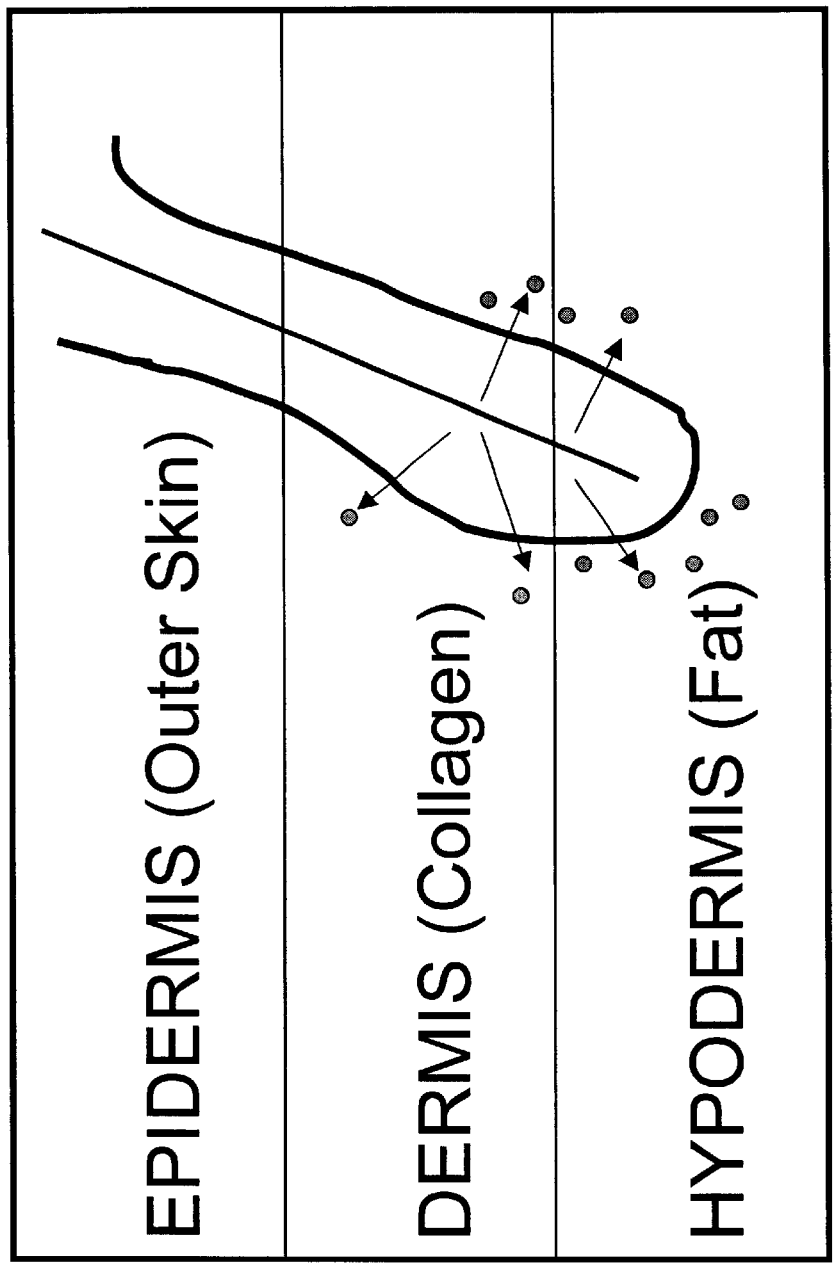
FIG. 7 is a schematic representation which shows the energy from the first laser pulse, which absorbed by the pigment within the hair gland, being transmitted as heat energy to the surrounding small blood vessels. These blood vessels are too small to be seen selectively by pulsed visible light.

FIG. 4 is a schematic representation of a pulse of visible light energy on the skin. The energy can be emitted either from a laser or intense pulsed light source. This light energy reaches into the collagen level of the skin and is captured by smaller blood vessels, which were augmented by a first infrared light energy pulse. The blood vessels have increased in size and become more accessible to absorbing visible light energy, due to the energy of the first infrared light energy pulse (which is absorbed by water, and thus indirectly augments the blood vessels within the collagen level of the skin). The second visible light energy pulse is configured to be absorbed by the hemoglobin ("red" color) within the vessels enhanced by the first light energy pulse. Therefore, the second visible light energy pulse has been effectively amplified by the first complementary infrared laser light energy pulse. Damage to the vessels with the collagen layer of the skin can then initiate an inflammatory response that therapeutically stimulates collagen remodeling and wrinkle removal.

Figure 8:
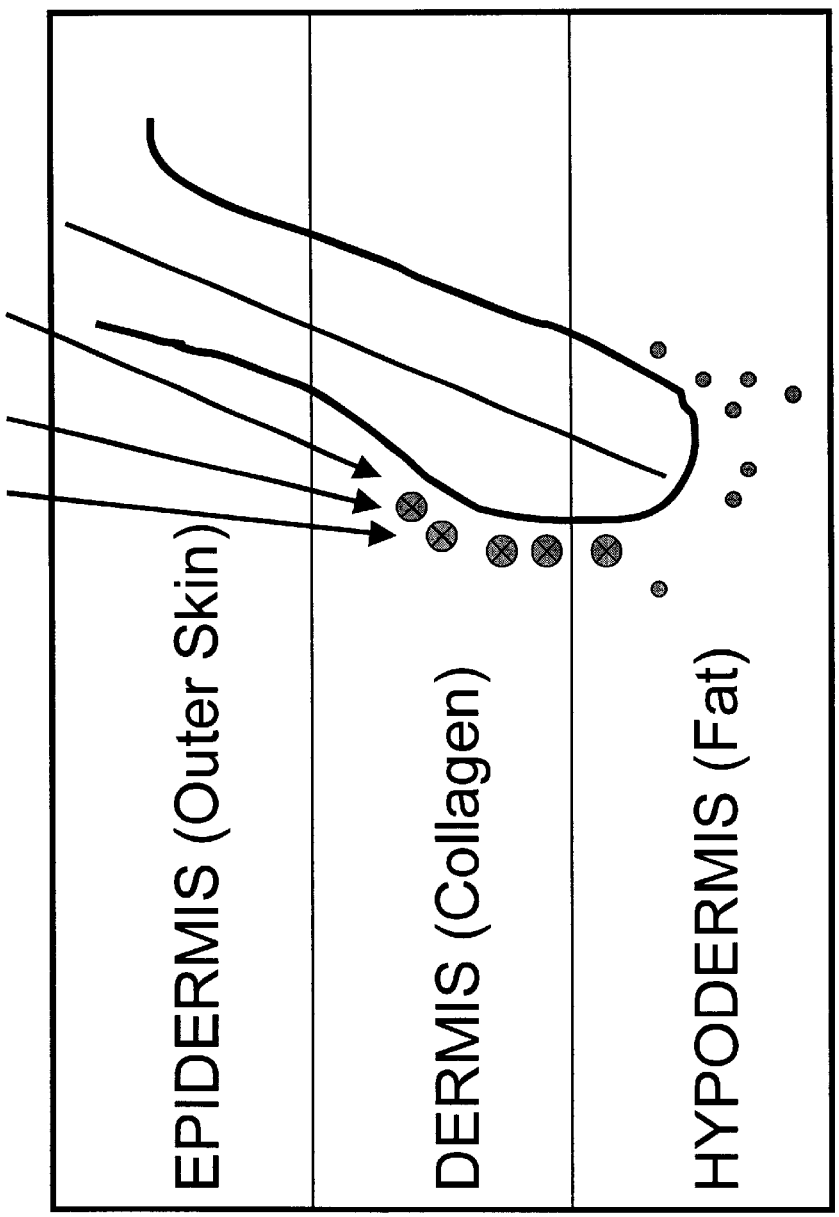
FIG. 8 is a schematic representation which shows how the effects are amplified by a subsequent pulse of visible light energy that is not targeting hair pigment or the hair gland directly, but is destroying the smaller blood vessels around the hair gland.

FIG. 8 is a schematic representation which shows how the effects are amplified by a subsequent pulse of visible light energy that is not targeting hair pigment or the hair gland directly, but is destroying the smaller blood vessels around the hair gland. These vessels were too small to be selectively treated before the effects of the first light pulse configured for the color of hair. The first light pulse enhanced the size of the vessels and made them selectively susceptible to the second light energy pulse, which is configured to the color and size of these vessels essential to the nourishment of the hair gland.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. I therefore claim as my invention all that comes within the scope and spirit of these claims.

I claim:

1. A method of altering a physical property of a region of skin, comprising:

applying a therapeutically effective amount of sensitizing light to the region, so that light energy is absorbed by the skin; and applying a therapeutically effective amount of treatment light to the region, wherein the treatment light is of a wavelength or wavelengths shorter than a wavelength or wavelengths of the sensitizing light;

wherein the application of the effective amount of the sensitizing light enhances an effect of the treatment light in altering the physical property of the region of the skin wherein the sensitizing light is applied in a at least one pulse of about 5 to about 7 msec in duration.

2. The method of claim 1, wherein the sensitizing light is applied in a series of consecutive pulses of about 5 to about 7 msec in duration.

3. A method of altering a physical property of a region of skin, comprising:

applying a therapeutically effective amount of sensitizing light to the region, so that light energy is absorbed by the skin; and applying a therapeutically effective amount of treatment light to the region, wherein the treatment light is of a wavelength or wavelengths shorter than a wavelength or wavelengths of the sensitizing light;

wherein the application of the effective amount of the sensitizing light enhances an effect of the treatment light in altering the physical property of the region of the skin, wherein applying the sensitizing light and applying the treatment light is separated by about 10 milliseconds to about 2 minutes.

4. The method of claim 3, wherein applying the sensitizing light and applying the treatment light is separated by at least about 20 milliseconds to about 1 minute.

5. A method of altering a physical property of a region of skin, comprising:

applying a therapeutically effective amount of sensitizing light to the region, so that light energy is absorbed by the skin; and applying a therapeutically effective amount of treatment light to the region, wherein the treatment light is of a wavelength or wavelengths shorter than a wavelength or wavelengths of the sensitizing light;

wherein the application of the effective amount of the sensitizing light enhances an effect of the treatment light in altering the physical property of the region of the skin, and wherein the treatment light is applied in at least one pulse of about 2 to about 4 msec in duration.

6. The method of claim 5, wherein the treatment light is applied in a series of pulses of about 2 to about 4 msec in duration.

7. A method of altering a physical property of a region of skin, comprising:

applying a therapeutically effective amount of sensitizing light to the region, so that light energy is absorbed by the skin; and applying a therapeutically effective amount of treatment light to the region, wherein the treatment light is of a wavelength or wavelengths shorter than a wavelength or wavelengths of the sensitizing light;

wherein the application of the effective amount of the sensitizing light enhances an effect of the treatment light in altering the physical property of the region of the skin, and wherein applying a therapeutically effective amount of the treatment light comprises applying multiple immediately sequential pulses of light of the treatment wavelength, wherein the multiple sequential pulses of light of the treatment wavelength are of substantially the same wavelength.

8. A method of altering a physical property of a region of skin, comprising:

applying a therapeutically effective amount of sensitizing light to the region, so that light energy is absorbed by the skin; and applying a therapeutically effective amount of treatment light to the region, wherein the treatment light is of a wavelength or wavelengths shorter than a wavelength or wavelengths of the sensitizing light;

wherein the application of the effective amount of the sensitizing light enhances an effect of the treatment light in altering the physical property of the region of the skin, wherein the change in the physical property is the removal of wrinkles or fine lines in the skin.

9. A method of altering a physical property of a region of skin, comprising:

applying a therapeutically effective amount of sensitizing light to the region, so that light energy is absorbed by the skin; and applying a therapeutically effective amount of treatment light to the region, wherein the treatment light is of a wavelength or wavelengths shorter than a wavelength or wavelengths of the sensitizing light;

wherein the application of the effective amount of the sensitizing light enhances an effect of the treatment light in altering the physical property of the region of the skin, wherein the change in the physical property is pigmentation removal.

10. A method of altering an appearance of a region of skin, comprising:

applying a therapeutically effective amount of light energy to the region of skin wherein the light energy applied has a wavelength of about 695 nanometers to about 1200 nanometers;

applying a therapeutically effective amount of intense pulsed light to the region of the skin, wherein the intense pulsed light is applied within minutes of the light energy, wherein the intense pulsed light applied has a wavelength of about 500 nanometers to about 600 nanometers;

wherein the application of the light energy results in a change in a physical property of the region of the skin that enhances an ability of the intense pulsed light to alter the appearance of the region of the skin, wherein the application of light energy results in an erythema of the region of skin that enhances susceptibility of the region of skin to the therapeutically effective amount of intense pulsed light.

11. A method of altering an appearance of a region of skin, comprising:

applying a therapeutically effective amount of light energy to the region of skin wherein the light energy applied has a wavelength of about 695 nanometers to about 1200 nanometers;

applying a therapeutically effective amount of intense pulsed light to the region of the skin, wherein the intense pulsed light is applied within minutes of the light energy, wherein the intense pulsed light applied has a wavelength of about 500 nanometers to about 600 nanometers;

wherein the application of the light energy and the intense pulsed light results in a change in a physical property of the region of the skin, wherein the region of skin has an initial temperature before application of light energy and applying light energy to the region of the skin comprises applying an amount of light energy sufficient to raise the temperature of the region of the skin from the initial temperature to a range of about 40° C. to about 45° C., wherein about 10 to about 20 joules of light energy is applied in a region of about 120 mm$^2$ area.

12. The method of claim 11, wherein about 18 to about 20 joules of light energy is applied in a region of about 120 mm$^2$ area.

13. The method of claim 11, wherein about 14 to about 18 joules of light energy is applied in a region of about 120 mm$^2$ area.

14. A method of altering an appearance of a region of skin, comprising:

applying a therapeutically effective amount of light energy to the region of skin wherein the light energy applied has a wavelength of about 695 nanometers to about 1200 nanometers;

applying a therapeutically effective amount of intense pulsed light to the region of the skin, wherein the intense pulsed light is applied within minutes of the light energy, wherein the intense pulsed light applied has a wavelength of about 500 nanometers to about 600 nanometers;

wherein the application of the light energy and the intense pulsed light results in a change in a physical property of the region of the skin, wherein the region of skin has an initial temperature before application of light energy and applying light energy to the region of the skin comprises applying an amount of light energy sufficient to raise the temperature of the region of the skin from the initial temperature to a range of about 40° C. to about 45° C.

wherein about 32 to about 40 joules of intense pulsed light is applied in a region of about 120 mm$^2$ area.

15. The method of claim 14, wherein intense pulsed light is applied as a doublet pulse of light.

16. The method of claim 14, wherein the change in the physical property of the skin is a change in a textural property of the region of skin.

17. The method of claim 16, wherein the textural property is the textural lines of the skin.

18. A method of altering an appearance of a region of skin, comprising:

applying a therapeutically effective amount of light energy to the region of skin wherein the light energy applied has a wavelength of about 695 nanometers to about 1200 nanometers;

applying a therapeutically effective amount of intense pulsed light to the region of the skin, wherein the intense pulsed light is applied within minutes of the light energy, wherein the intense pulsed light applied has a wavelength of about 500 nanometers to about 600 nanometers;

wherein the application of the light energy and the intense pulsed light results in a change in a physical property of the region of the skin, wherein the region of skin has an initial temperature before application of light energy and applying light energy to the region of the skin comprises applying an amount of light energy sufficient to raise the temperature of the region of the skin from the initial temperature to a range of about 40° C. to about 45° C.

19. A method of removing a hair in skin, comprising applying light energy with a wavelength of about 700 nanometers for about 2 milliseconds to about 800 milliseconds, wherein the light energy is applied to the skin;

subsequently applying pulsed light to the skin, wherein the pulsed light is applied within fifteen minutes of applying the light energy, and wherein the pulsed light is visible light;

wherein the application of the light energy enhances the effect of the pulsed light in the removal of the hair from the skin.

20. The method of claim 19, wherein the pulsed light applied to the skin is applied in at least two pulses of between 2 to 7 milliseconds in duration.

21. A method of removing a hair in skin, comprising applying light energy with a wavelength of about 700 nanometers for about 2 milliseconds to about 800 milliseconds, wherein the light energy is applied to the skin;

applying pulsed light to the skin, wherein the pulsed light is applied within fifteen minutes of applying the light energy, and wherein the pulsed light is visible light;

wherein the application of the light energy and the pulsed light results in the removal of the hair from the skin, and wherein the two pulses are separated by at least one minute.

22. A method of altering an appearance of a region of skin, comprising:

applying a therapeutically effective amount of light energy to the region of skin wherein the light energy applied has a wavelength of about 695 nanometers to about 1200 nanometers;

applying a therapeutically effective amount of intense pulsed light to the region of the skin, wherein the intense pulsed light is applied within minutes of the light energy, wherein the intense pulsed light applied has a wavelength of about 500 nanometers to about 600 nanometers;

wherein the application of the light energy and the intense pulsed light results in a change in a physical property of the region of the skin, wherein about 32 to about 40 joules of intense pulsed light is applied in a region of about 120 mm$^2$ area, and the intense pulsed light is applied as a doublet of light, and the doublet pulse of light is applied as a primary pulse of at least 3 milliseconds and a secondary pulse of at least 4 milliseconds, with a delay of about 5 to about 15 milliseconds between the primary pulse and the secondary pulse.

* * * * *